United States Patent [19]
Bosma et al.

[11] Patent Number: 5,908,403
[45] Date of Patent: Jun. 1, 1999

[54] DRAINAGE CATHETER WITH HEMOSTATIC DEVICE

[75] Inventors: Gjalt Bosma, Opeinde; Tiemen Noppert, Muntendam, both of Netherlands

[73] Assignee: Cordis Europa, N.V., Poden, Netherlands

[21] Appl. No.: 08/852,196

[22] Filed: May 6, 1997

[30] Foreign Application Priority Data

May 7, 1996 [NL] Netherlands ............. 1003056

[51] Int. Cl.$^6$ .................................................. A61M 3/00
[52] U.S. Cl. ......................................................... 604/43
[58] Field of Search ..................... 604/30, 31, 33, 604/43, 246, 249

[56] References Cited

U.S. PATENT DOCUMENTS

| | | | |
|---|---|---|---|
| 4,715,848 | 12/1987 | Beroza ........................... | 604/43 |
| 5,244,459 | 9/1993 | Hill ................................ | 604/33 |
| 5,247,966 | 9/1993 | Stevens et al. . | |
| 5,320,599 | 6/1994 | Griep et al. . | |
| 5,395,315 | 3/1995 | Griep .............................. | 604/43 |
| 5,453,088 | 9/1995 | Boudewijn et al. ............ | 604/43 |
| 5,713,851 | 2/1998 | Boudewijn et al. ............ | 604/43 |
| 5,722,949 | 3/1998 | Sanese ........................... | 604/249 |

FOREIGN PATENT DOCUMENTS

| | | |
|---|---|---|
| 0 576 380 | 12/1993 | European Pat. Off. . |
| 0 654 275 | 5/1995 | European Pat. Off. . |
| 0 693 295 | 1/1996 | European Pat. Off. . |
| 2117 497 | 10/1983 | United Kingdom . |
| WO 93/05826 | 4/1993 | WIPO . |

Primary Examiner—John D. Yasko
Assistant Examiner—Manuel Mendez
Attorney, Agent, or Firm—Michael W. Montgomery

[57] ABSTRACT

A drainage catheter comprises a tubular basic catheter body defining separate catheter lumens respectively comprising a pressure channel and a discharge channel. Connectors are provided at the proximal end of the catheter for respectively connecting the pressure channel to a source of liquid under pressure and the discharge channel to a discharge receptacle. An inlet opening is positioned in the side of the catheter adjacent the distal end thereof. The discharge channel communicates with the inlet opening, while the pressure channel extends from the proximal and distally forward of the inlet opening and then curves rearwardly to join the discharge channel at the inlet opening. The catheter also includes a first normally-closed valve positioned within the pressure channel and a second normally closed valve positioned within the discharge channel and an actuator coupled to both the first and second valves so that the valves may be simultaneously moved from their normally closed positions to open positions for the operation of the catheter.

7 Claims, 2 Drawing Sheets

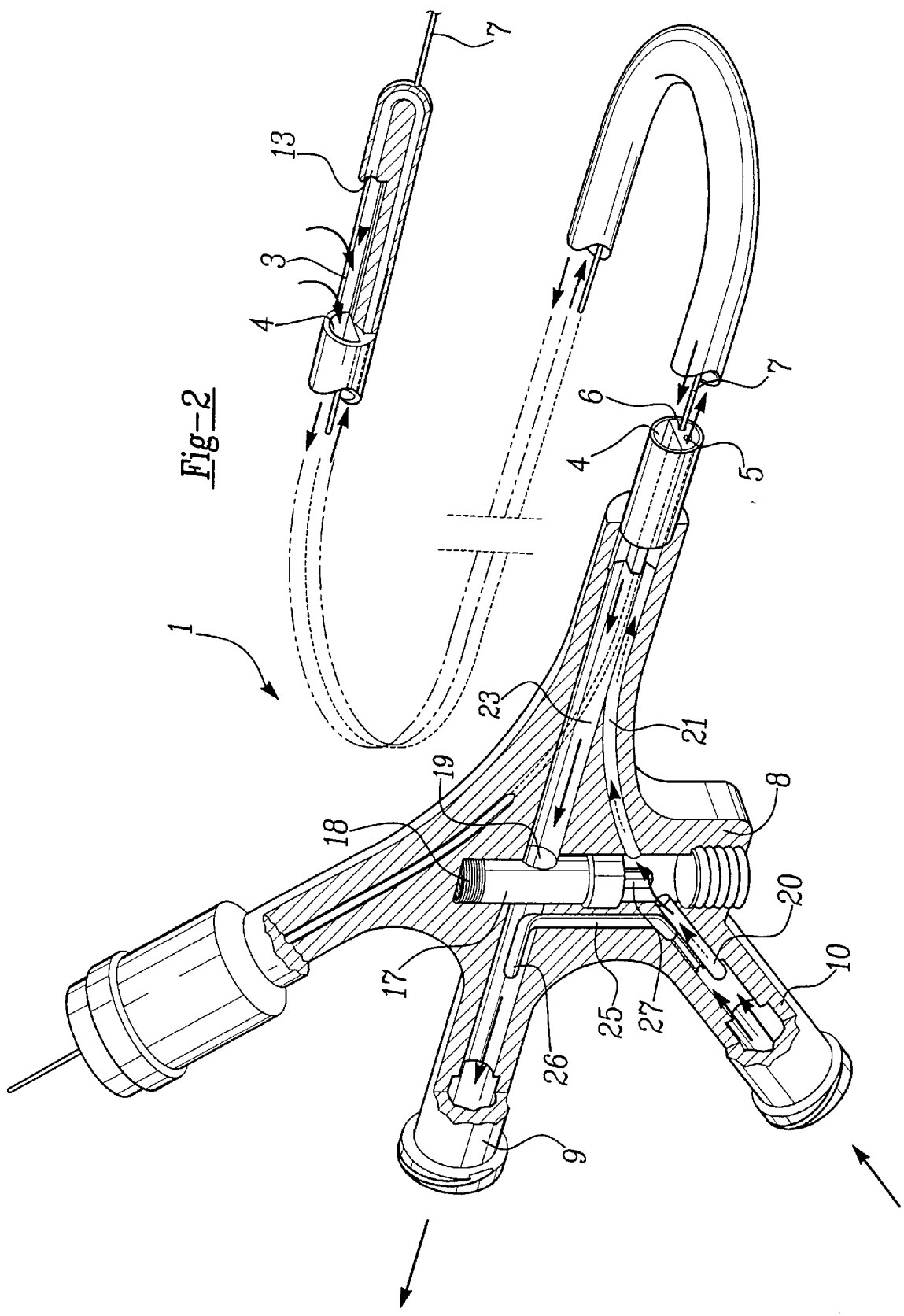

DRAINAGE CATHETER WITH HEMOSTATIC DEVICE

BACKGROUND OF THE INVENTION

1. Field of the Invention

The present invention relates to a drainage catheter having a catheter body with a pressure channel, or lumen, and a discharge channel, or lumen. The catheter has a connector at the proximal end of the catheter for connecting the pressure channel and the discharge channel to a source of liquid under pressure and discharge container, respectively, and may be used for removing blood clots, plaque and other debris from vessels of the body.

2. Description of the Prior Art

In one form of a drainage catheter a pressure channel extends along the catheter and distally forms a tongue at the front end of the catheter, then curves back to a discharge channel. A spray nozzle is formed in the tongue, to deliver a liquid jet of fluid through the distal end of the discharge channel. The jet of fluid which is delivered by the spray nozzle is used for sucking, breaking up, crushing and transport of solid particles and for removing the solid particles, or deposits, from the vessels of the body of a patient.

The present invention has for its object a drainage catheter system of the type described above which is simpler and safer to use, can be introduced into blood vessels without damaging the vascular system. Specifically, the catheter of this invention may be used without the concern of excessive blood being drawn out of the body.

SUMMARY OF THE INVENTION

With this invention, a drainage catheter is provided which comprises a cylindrical catheter body, having a pair of separate lumens defined within the body to form a mutually separate pressure channel and a discharge channel extending the length of the catheter. Connecting means are provided at the proximal end of the catheter for connecting the pressure channel and the discharge channel to, respectively, a source of pressurized liquid and to discharge container.

At the distal end of the catheter, the discharge channel defines an inlet opening which is formed in a side wall of the catheter body. The pressure channel is also defined within the body to extend forwardly toward the distal end beyond the inlet opening, and then to reversely bend approximately 180 degrees, to extend again a short distance rearwardly. Spray nozzle means is provided to direct a liquid jet from the pressure channel to the discharge channel adjacent the inlet opening, to cause a suction to be created through the inlet opening by aspiration, or by ejector action. Thus, suction occurs at the location of the side inlet opening. Preferably, the spray nozzle is constricted by a tapered nozzle and is positioned distal from the side inlet opening.

A source of liquid under pressure can thus suffice for the operation of the catheter, so that suction pump is generally superfluous. Only with very long and thin catheters might a suction device still be used to augment the suction. During use, the feed of the liquid under pressure may be controlled as to pressure, or flow rate, with the suction generated being directly dependent on this feed. With the catheter according to the invention, liquids, soft deposits, and solid particles of a size permitting passage through the inlet opening may be removed from the body.

Preferably, in the catheter of this invention there is formed adjacent the distal end at least one narrow passage opening in an outer wall portion of the body on a side remote from the inlet opening, and communicating between the pressure channel and the exterior. Thus, during use, a small quantity of fluid under pressure from the pressure channel may pass into the vicinity of the front end of the catheter by way of the narrow passage opening.

Preferably, the catheter carries adjacent its distal end a rigid J or U-shaped tube which is sealingly positioned with at least one leg of the U-shaped tube in the pressure channel, and with a second leg thereof communicating with the discharge channel. The end of the second leg of the U-shaped tube is positioned adjacent to and preferably generally upstream of the inlet opening. Thus, the U-shaped channel defines the reverse bending portion of the flow path described above and also the nozzle where the discharge channel and the pressure channel meet adjacent the distal end. Thus, the cross-sectional shape of the pressure channel in the reversely bending portion and the nozzle may in this way be very precisely controlled and dimensioned, such that the flow of the liquid under pressure out of the pressure channel and past the inlet opening can create the precisely desired aspiration or ejector action with great reliability. Typically the U-shaped tube is made of a metal such as stainless steel.

Preferably, the second leg of the U-shaped tube is narrowed toward its free end, positioned adjacent the inlet opening so as to form a jet nozzle for creation of effective suction pressure by the aspiration effect as rapidly moving pressurized fluid passes across the inlet opening and down the discharge channel. Even with catheters having a very small diameter, a reliable suction action by aspiration may be obtained in this manner.

It is preferable for the pressure channel to be connected at its proximal end to a pressurized source of liquid, while the discharge channel is connected at its proximal end to a receptacle, for waste fluid received from the discharge channel.

Also, the drainage catheter of the present invention includes a normally-closed fluid valve which is positioned in the discharge channel, or lumen, and a normally-closed fluid valve which is positioned in the pressure channel. An actuator is coupled to both of the valves so that when the pressure valve is opened to permit fluid pressure to be applied through the pressure channel to the spray nozzle, the discharge valve is simultaneously opened to permit flow through to the discharge channel. Accordingly, blood is prevented from leaving the body until fluid pressure is applied.

In another embodiment of the invention, the actuator is initiated to open both valves upon the application of fluid pressure to the pressure channel. In other words, when fluid pressure is applied to the pressure channel it causes the valve in the pressure channel to open thereby causing the valve in the discharge channel to open simultaneously.

The invention may be better understood by the following description with reference to the figures of the preferred embodiment.

DESCRIPTION OF THE PREFERRED EMBODIMENT

Figure 1:
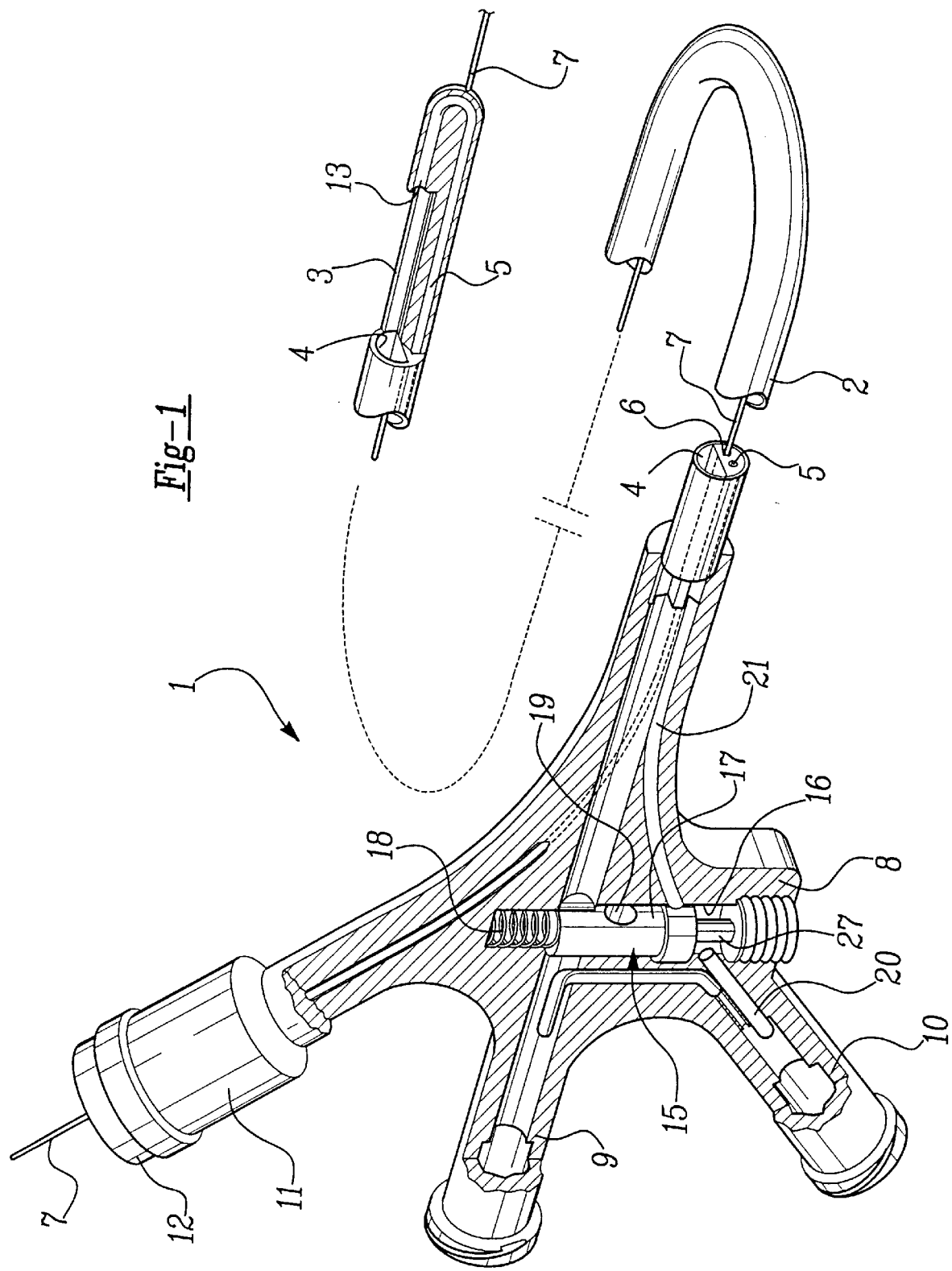
FIG. 1 illustrates in a partly broken away perspective view a preferred embodiment of the drainage catheter of the invention with the fluid valves in their normally closed positions; and, FIG. 2 shows a view corresponding to FIG. 1 with the fluid valves in an open position.

The catheter 1 illustrated in FIG. 1 comprises a cylindrical or tubular body 2. Three lumens have been formed inside the catheter body 2; a pressure lumen 5, a discharge lumen 4 and a guidewire lumen 6.

At the distal end of the catheter body 2 is an opening 3 which has been formed and is connected with a discharge lumen 4. At the distal end for the catheter the pressure lumen 5 terminates in a jet nozzle 13. Liquid under pressure supplied via the pressure lumen 5 leaves the jet nozzle 13 in the form of a powerful jet, which is directed inward along the opening 3 in the discharge lumen 4. With this jet flow there will be an ejector action which generates a suction at the opening 3, which will cause the removal of blood clots through the discharge lumen 4. When positioning the catheter 1, the guidewire lumen 6 is used for the passage of the guidewire 7.

At the proximal end for the catheter 1 a connecting member 8 has been arranged, inside of which the connections with the lumens have been received. For the sake of clarity this connecting member 8 has been illustrated in FIG. 1 while rotated, in relating to the basic body 2, a quarter turn to the left. By way of channel 23 in the connecting member 8, the discharge lumen 4 is connected with the discharge connection 9. The pressure lumen 5 is connected with a pressure connection 10 by way of channel sections 20 and 21. The guidewire channel 7 is connected with the guidewire connection 11. This guidewire connection 11 has been provided with an anti-hemostatic device 12, which prevents blood from flowing out through the guidewire channel while using the catheter 1. The discharge connection 9 and the pressure connection 10 have both been provided with Luer-lock connections. Inside the connecting member 8 valve means 15 have been received which can open and close the pressure lumen and the discharge lumen simultaneously.

With the preferred example of an embodiment illustrated, the valve means 15 comprise a slide 17, movable to and fro, received inside a channel 16 formed inside the connecting member. The channel 16 has been closed off with a plug 22. As can be seen in the figures, the slide 17 is, at its end turned away from the screw plug 22, acted upon by a helical spring 18. The latter pushes the slide 17 into the closed position illustrated in FIG. 1, in which both the discharge lumen and the pressure lumen have been blocked. The slide has been provided with a distance pin 27 with which the slide 17 is positioned against the screw plug 22 when closed.

As can be seen in FIG. 1, in closed position the slide 17 leaves the relatively proximal section 20 of the pressure lumen free and closes the relatively distal section 21 of the pressure lumen off. In this sate consequently no blood can leak through the discharge lumen 4 or the pressure lumen 5 from the connections 9, 10 respectively.

As the relatively proximal section 20 of the pressure lumen is connected to that side of the slide 17 opposite to the side of the slide which is acted upon by the spring 18, the slide 17 will be pushed upwards against the force exerted by the spring 18, when via the pressure connection 10 liquid under pressure is supplied.

In the open position illustrated in FIG. 2, a transverse channel 19 in the slide 17 has been moved in line with the channel 23 inside the connecting member 8, forming the continuation of the discharge lumen 4. The cross-section of the transverse channel 19 is equal to the cross-section of the channel 23, so that in the open position there will be no resistance to flow. The material is drawn through the opening 3 and is removed freely through the discharge lumen 4 and the channel section 23 from the discharge connection 9.

At the same time the discharge lumen 4 is opened the slide 17 is moved away from the entrance of the relatively distal section 21 of the pressure lumen, so that the liquid under pressure supplied via the connection 10 can flow freely through the relatively proximal section 20 to the relatively distal section 21 and then through the pressure lumen 5 to the jet nozzle 13.

To assist the flow in the discharge lumen an auxiliary pressure channel 25 has been formed in the connecting member 8 of which the outlet 26 is directed towards the connecting member 9. By way of this auxiliary pressure channel 25, part of the liquid under pressure supplied through the pressure connection 10 flows away in the direction indicated by the arrows, as a result of which a liquid jet is formed at the outlet 26 of the auxiliary pressure channel 25, reinforcing the flow in the discharge lumen 4 as referred to above.

As soon as the supply of liquid under pressure through the pressure connection 10 is closed off, the slide 17 will be pushed into the closed position illustrated in FIG. 1 due to the action of the spring 18, and at the same time the pressure lumen and the discharge lumen are closed off, so that no blood can then be drawn out of the body in this "closed" position.

The invention is of course not limited to the preferred embodiment as shown in the figures and as described in the specification. The description has been offered for illustrative purposes only and is not intended to limit the scope of the invention, which is as defined by the claims below:

That which is claimed is:

1. A drainage catheter which comprises:
    a flexible, tubular basic catheter body defining first and second catheter lumen respectively comprising a pressure channel and a discharge channel;
    a connector at a proximal end of said catheter for respectively connecting the pressure channel to a source of liquid under pressure, and the discharge channel to a discharge port;
    an inlet opening positioned in the side wall of said catheter adjacent the distal end thereof, said discharge channel communicating with said inlet opening, said pressure channel extending from said proximal end to a point distal of said inlet opening and then curving rearwardly to join said discharge channel at said inlet opening, said pressure channel defining a spray nozzle to direct pressurized fluid in the pressure channel across said inlet opening and into said discharge channel to create a suction adjacent said inlet opening,
    a first normally-closed valve positioned along the pressure channel, a second normally-closed valve positioned along the discharge channel, and
    an actuator coupled to both said first and second valve so that said actuator is adapted to cause said first and second valves to simultaneously move from the normally-closed positions to open positions.

2. A drainage catheter as defined in claim 1, which includes a pressure detector positioned in communication with the pressure channel which, upon sensing an increase in pressure in the pressure channel, causes the actuator to open the first and second normally-closed valves.

3. A drainage catheter as defined in claim 2, wherein said first and second valves are each formed of a movable bar which intersects the pressure channel and discharge channel respectively in a direction approximately transverse to the axis of the pressure channel and discharge channel respectively; each movable bar being formed such that when the movable bar is in a first position the bar resists flow of fluid through the pressure channel and the discharge channel respectively, and when each movable bar is moved to a second position the movable bar is adapted to permit substantially unrestricted flow of fluid through the pressure channel and discharge channel respectively.

4. A drainage catheter as defined in claim 3, wherein each of the movable bars are slidably mounted to move in a direction approximately transverse to the axis of the pressure channel and discharge channel respectively.

5. A drainage catheter as defined in claim 4, wherein said movable bars are directly connected to each other, the actuator being connected to one of the movable bars so that said actuator causes both of the movable bars to slide simultaneously.

6. A drainage catheter as defined in claim 5, including a spring positioned at one end of the directly connected movable bars to bias the movable bars in a closing direction to cause the first and second valves to be normally biased toward closed positions.

7. A drainage catheter as defined in claim 6, wherein the actuator comprises a cylindrical member, one of the movable bars takes the form of a cylindrical piston which slidably engages the cylindrical member, and the cylindrical member intersects the pressure channel, so that when the fluid pressure in the pressure channel increases the cylindrical piston is caused to move, thereby causing both of the first and second valves to move from normally-closed positions to open positions.

* * * * *

UNITED STATES PATENT AND TRADEMARK OFFICE
CERTIFICATE OF CORRECTION

PATENT NO. : 5,908,403
DATED : June 1, 1999
INVENTOR(S) : Bosma, et al.

It is certified that error appears in the above-identified patent and that said Letters Patent is hereby corrected as shown below:

On the title page item

[73]    Assignee:    Cordis Europa, N.V. Poden, Netherlands should be:

Cordis Europa, N.V. Roden, Netherlands

Signed and Sealed this

Twenty-eighth Day of November, 2000

Attest:

Q. TODD DICKINSON

Attesting Officer

Director of Patents and Trademarks